United States Patent
Wang et al.

(10) Patent No.: US 8,394,630 B2
(45) Date of Patent: Mar. 12, 2013

(54) PRODUCING A MAMMALIAN PLURIPOTENT CELL POPULATION FROM MAMMALIAN BLASTOMERE-LIKE STEM CELLS (BLSCS)

(75) Inventors: James Wang, Monterey Park, CA (US); Yun Yen, Arcadia, CA (US)

(73) Assignee: StemBios Technologies, Inc., Monterey Park, CA (US)

( * ) Notice: Subject to any disclaimer, the term of this patent is extended or adjusted under 35 U.S.C. 154(b) by 111 days.

(21) Appl. No.: 12/686,584

(22) Filed: Jan. 13, 2010

(65) Prior Publication Data

US 2010/0183570 A1 Jul. 22, 2010

Related U.S. Application Data

(60) Provisional application No. 61/144,206, filed on Jan. 13, 2009.

(51) Int. Cl.
*C12N 15/02* (2006.01)
(52) U.S. Cl. .................. 435/377; 435/384; 435/387
(58) Field of Classification Search ................ None
See application file for complete search history.

(56) References Cited

U.S. PATENT DOCUMENTS

| | | |
|---|---|---|
| 2002/0115059 A1 | 8/2002 | Terada et al. |
| 2005/0255588 A1 | 11/2005 | Young et al. |
| 2008/0305079 A1 | 12/2008 | Chen |

FOREIGN PATENT DOCUMENTS

| | | |
|---|---|---|
| WO | WO2006/070370 | 7/2006 |
| WO | WO2007/026353 | 3/2007 |
| WO | WO2007/100845 | 9/2007 |

OTHER PUBLICATIONS

Amit et al. Feeder Layer- and Serum-Free Culture of Human Embryonic Stem Cells. Biology of Reproduction, 2004, vol. 70, 837-845.*
Schuldiner et al. Effects of eight growth factors on the differentiation of cells derived from human embryonic stem cells. PNAS, 2000, vol. 97, pp. 11307-11312.*
http://stemcells.nih.gov/info/glossary.asp.*
Serafini et al. "Myeloid Suppressor Cells in Cancer: Recruitment, Phenotype, Properties, and Mechanisms of Immune Suppression" Seminars in Cancer Biology; 16:53-65 (2006).
Dolcetti et al. "Myeloid-Derived Suppressor Cell Role in Tumor-Related Inflammation" Cancer Letters; 267:216-225 (2008).
Talmadge "Pathways Mediating the Expansion and Immunosuppressive Activity of Myeloid-Derived Suppressor Cells and Their Relevance to Cancer Therapy" Clin. Cancer Res.; 13918):5243-5248 (2007).
Gabrilovich et al. "Myeloid-Derived-Suppressor Cells as Regulators of the Immune System" Nat. Rev. Immunol; 9(3):162-174 (2009).
Ostrand-Rosenberg et al. "Myeloid-Derived Suppressor Cells: Linking Inflammation and Cancer" J. Immunol.; 182:4499-4506 (2009).

* cited by examiner

*Primary Examiner* — Deborah Crouch
(74) *Attorney, Agent, or Firm* — Occhiuti Rohlicek & Tsao LLP

(57) ABSTRACT

Disclosed are novel stem cells of non-embryonic origins and the uses thereof.

12 Claims, 13 Drawing Sheets

Purification of BLSC from Hemolysis - (BLSC counts 200x10⁶ cells/ml)

Fl1: CD10-FITC
Fl2: CD66e-PE
Fl4: CD90-APC

Purification of BLSC from plasma fraction – (BLSC counts 239x10$^6$ cells/ml)
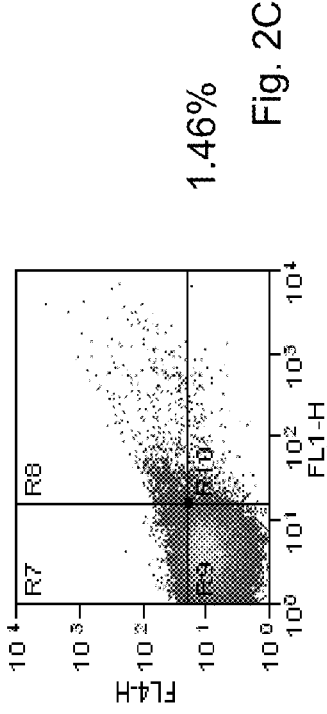
Fig. 2B
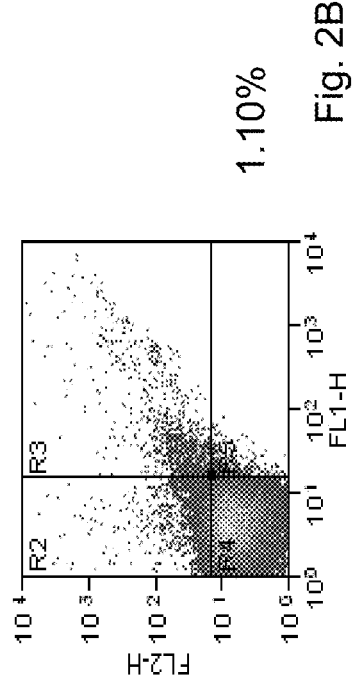
Fig. 2A
Fig. 2C
Fl1: CD10-FITC
Fl2: CD66e-PE
Fl4: CD90-APC BLSCs cultured- formation multi-layers, mesh-net structure (200x)

BLSC cultured: Aggregation

200x

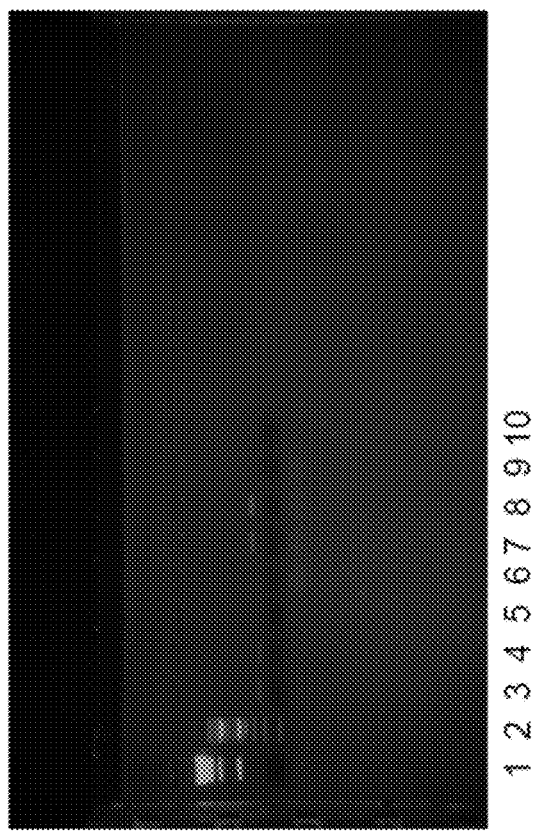

RT-PCR result of SBR, SBT and BLSC:
Has RNA expression in SBR and SBT for beta-actin and GAPDH;
No RNA expression in BLSC for beta-actin and GAPDH

FIG. 13

Lane 1: 1 Kb marker. Lane 2: 100bp marker. Lane 3: SBR RNA for beta-actin primer
Lane 4: SBT RNA for beta-actin primer. Lane 5: BLSC RNA for beta-acin primer
Lane 6: No RNA, only beta-acin primer. Lane 7: SBR RNA for GAPDH primer
Lane 8: SBT RNA for GAPDH primer. Lane 9: BLSC RNA for GAPDH primer
Lane 10: No RNA, only GAPDH primer

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic primer

<400> SEQUENCE: 1
acaaaaccta acttgcgcag                                        20

<210> SEQ ID NO 2
<211> LENGTH: 20
<212> TYPE: DNA
<213> ORGANISM: Artificial Sequence
<220> FEATURE:
<223> OTHER INFORMATION: Synthetic primer

<400> SEQUENCE: 2
tcctgtaaca acgcatctca                                        20

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
agccacatcg ctcagacacc                                        20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
gtactcagcg gccagcatcg                                        20

PRODUCING A MAMMALIAN PLURIPOTENT CELL POPULATION FROM MAMMALIAN BLASTOMERE-LIKE STEM CELLS (BLSCS)

CROSS-REFERENCE TO RELATED APPLICATIONS

This application claims the priority of U.S. Application No. 61/144,206, filed on Jan. 13, 2009. The contents of the application are hereby incorporated by reference in its entirety.

BACKGROUND

Totipotent stem cells, such as embryonic stem (ES) cells, can differentiate in vivo into all cell lineages, and, when induced in vitro, differentiate into most cell types. ES cells are derived from early mammalian embryos. Due to their totipotency, they are believed to hold a great promise for treating degenerative or inherited diseases. However, ethical and logistical considerations have hampered the use of human ES cells in research and therapy. Totipotent or pluripotent stem cells of non-embryonic origins (e.g., from tissues of adult or young animals) would circumvent this obstacle. Although some stem cells have been obtained from such non-embryonic origins, some of these cells have limited developmental potentials. Also, logistically, these cells are difficult to obtain and amounts of the cells are too limited to meet meaningful clinical or research uses. Furthermore, some of the cells can develop into teratoma in vivo and therefore are not desired for in vivo uses. There is a need for non-embryonic totipotent or pluripotent stem cells that are safer and easy to obtain, and have an abundant source.

SUMMARY

This invention is based on, at least in part, an unexpected discovery that a population of stem cells prepared from non-embryonic origins are totipotent or pluripotent, can be obtained at a very high yield, and do not develop into teratoma in vivo.

Accordingly, one aspect of this invention features a method of making a pluripotent or totipotent stem cell population. The method includes obtaining a plurality of blastomere-like stem cells (BLSCs), culturing the BLSCs in a medium containing retinoic acid (RA) or transforming growth factor beta (TGF-β), and identifying and enriching pluripotent or totipoent cells among the cultured cells. The pluripotent or totipoent cells express the mRNA of GAPDH or beta-actin. In other words, the level of mRNA of GAPDH or beta-actin is detectable by the RT-PCR assay in the manner described in the example section below.

The pluripotent or totipoent stem cells are generally 1 to 15 micrometers in size, preferably 1 to 10 micrometers in size, and more preferably 1 to 5 micrometers in size. These sizes are those of the cells that are in suspension or attachment (i.e., suspended cells or attached cells).

The term "stem cell" refers to a cell that is capable of differentiating into a number of final, differentiated cell types. Stem cells may be totipotent or pluripotent. Totipotent stem cells typically have the capacity to develop into any cell type. Totipotent stem cells can be both embryonic and non-embryonic in origin. Pluripotent cells are typically cells capable of differentiating into several different, final differentiated cell types. Unipotent stem cells can produce only one cell type, but have the property of self-renewal which distinguishes them from non-stem cells. These stem cells can originate from various tissue or organ systems, including, but not limited to, blood, nerve, muscle, skin, gut, bone, kidney, liver, pancreas, thymus, and the like. In accordance with the present invention, the stem cell is derived from an adult or neonatal tissue or organ. BLSC, which will be described in detail below, are a population of non-embryonic stem cells in adult or young animals. These cells are totipotent and have the differentiation capability similar to that of embryonic stem cells. See WO2007/100845

Cells obtained by culturing BLSCs in an RA-containing medium are named SBR. In one embodiment, the medium contains 0.1 to 20 µM RA and the BLSCs can be cultured for 2 to 8 weeks. In another embodiment, the medium contains 1 to 15 µM RA and the BLSCs are cultured for 2 to 8 weeks. In yet another embodiment, the medium contains 5 to 12 µM RA and the BLSCs are cultured for 3 to 4 weeks. The pluripotent or totipoent SBR cells thus prepared are 1 to 15 micrometers (such as 1 to 10, 1 to 5, 2 to 5, or 3 to 5 micrometers) in size and can form a sheet-like structure in suspension.

Cells obtained by culturing BLSCs in a medium containing TGF-β are named SBT. In one embodiment, the medium contains 1 to 40 nM TGF-β and the BLSCs are cultured for 2 to 8 weeks. In another embodiment, the medium contains 2 to 20 nM TGF-β and the BLSCs are cultured for 2 to 8 weeks. In yet another embodiment, the medium contains 5 to 12 nM TGF-β and the BLSCs are cultured for 4 to 6 weeks. The pluripotent or totipoent SBT cells are 1 to 15 micrometers (such as 1 to 10, 1 to 5, 2 to 5, or 3 to 5 micrometers) in size, have a round shape, and can form aggregation.

Another aspect of this invention features a composition containing a plurality of the above mentioned cultured cells, which are (1) are pluripotent or totipotent, (2) are 1-15 micrometers in size, and (3) express the mRNA of GAPDH or beta-actin. The cells can be prepared by the method described above. The composition can further contain RA or TGF-β. In one embodiment, the cells are $CD10^+$, $CD90^+$, $CD105^+$, and $CXCR4^+$. In another embodiment, the cells are trypan blue staining negative. That is, the cells show trypan blue exclusion. In yet another embodiment, the cultured cells contain a first population of the cells that are $CD66e^+$ and a second population of the cells that are $CD66e^-$.

The cells are substantially pure. The term "substantially pure", when used in reference to stem cells or cells derived therefrom (e.g., differentiated cells), means that the specified cells constitute the majority of cells in the preparation (i.e., more than 20%, 30%, 40%, 50%, 60%, 70%, 80%, 90%, or 95%). Generally, a substantially purified population of cells constitutes at least about 70% of the cells in a preparation, usually about 80% of the cells in a preparation, and particularly at least about 90% of the cells in a preparation (e.g., 95%, 97%, 99% or 100%). As such, a method of the invention provides the advantage that a substantially pure population of a particular type of cells (e.g., SBR or SBT cells) can be obtained without contamination by other cell types.

The just described cultured cells can be used to express exogenous, recombinant polypeptide. Thus, within the scope of this invention are such cultured cells, each of which includes a recombinant nucleic acid. The recombinant nucleic acid can encode a polypeptide and the cell can contain an mRNA encoding the polypeptide.

The described cultured cells can be genetically manipulated so that they do not express the beta2-microglobulin gene or do not express one or more proteins encoded by the class I major histocompatibility complex (MHC) genes that elicit a T lymphocyte mediated reaction against the cell. These cells can be used as universal donor cells since they do not lead to host rejections of grafts.

In one aspect, the invention features a method of treating a degenerative disease in a subject. The method includes administering to a subject in need thereof an effective amount of the above-described composition, which contains one or more of the above-described pluripotent or totipoent cells. In one embodiment, at least one of the cells includes a recombinant nucleic acid. The recombinant nucleic acid can encode a polypeptide and the cell can contain an mRNA encoding the polypeptide. Examples of the degenerative disease include diabetes, a neurodegenerative disease, arthritis, and cancer. Examples of the neurodegenerative disease include Parkinson's disease.

In another aspect, the invention features a method of treating an autoimmune disease in a subject. The method includes administering to a subject in need thereof an effective amount of the above-described composition.

A subject to be treated for one of the above-described disorders can be identified by standard diagnosing techniques for that particular disorder. "Treating" refers to administration of a composition (e.g., a cell composition) to a subject, who is suffering from or is at risk for developing that disorder, with the purpose to cure, alleviate, relieve, remedy, delay the onset of, prevent, or ameliorate the disorder, the symptom of the disorder, the disease state secondary to the disorder, or the predisposition toward the damage/disorder. An "effective amount" refers to an amount of the composition that is capable of producing a medically desirable result in a treated subject. The treatment method can be performed alone or in conjunction with other drugs or therapies.

In yet another aspect, the invention features a method for identifying a drug candidate for treating a degenerative disease. The method includes the steps of contacting a test compound with the above-described composition or cells and determining the expression level of a polypeptide that is down-regulated in the degenerative disease. The expression level in the presence of the test compound, if higher than that in the absence of the compound, indicates that the compound is a candidate for treating the disease. Examples of the degenerative diseases include diabetes, a neurodegenerative disease, arthritis, cancer, or an autoimmune disorder. The expression level can be determined at either the mRNA level or at the protein level.

In yet another aspect, the invention features a method for introducing a heterologous nucleic acid in a subject. The method includes the steps of obtaining the above-described composition or cells, where at least one of the cells includes a heterologous nucleic acid, and administering the cell into a subject in need thereof. The heterologous nucleic acid can encode a polypeptide. Once administered, the cell expresses the polypeptide in the subject.

The term "heterologous" is a relative term, which when used with reference to portions of a nucleic acid indicates that the nucleic acid comprises two or more subsequences that are not found in the same relationship to each other in nature. For instance, a nucleic acid that is recombinantly produced typically has two or more sequences from unrelated genes synthetically arranged to make a new functional nucleic acid, e.g., a promoter from one source and a coding region from another source. The two nucleic acids are thus heterologous to each other in this context. When added to a cell, the recombinant nucleic acids would also be heterologous to the endogenous genes of the cell. Thus, in a chromosome, a heterologous nucleic acid would include a non-native (non-naturally occurring) nucleic acid that has integrated into the chromosome, or a non-native (non-naturally occurring) extrachromosomal nucleic acid. In contrast, a naturally translocated piece of chromosome would not be considered heterologous in the context of this patent application, as it comprises an endogenous nucleic acid sequence that is native to the mutated cell. Similarly, a heterologous protein indicates that the protein comprises two or more subsequences that are not found in the same relationship to each other in nature (e.g., a "fusion protein," where the two subsequences are encoded by a single nucleic acid sequence). Such protein can be generated by recombinant techniques.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (naturally occurring) form of the cell or express a second copy of a native gene that is otherwise normally or abnormally expressed, under expressed or not expressed at all.

Within the scope of this invention is a cell bank or library having a plurality of above-described composition, each containing a population of pluripotent or totipoent cultured cells. The cells can be human cells or non-human cells. The bank can be produced by harvesting cells from a plurality of subjects to obtain a plurality of BLSCs populations, respectively; characterizing the cell populations to obtain at least one predetermined characteristic for each, and cataloguing each of the cell populations according to the at least one predetermined characteristic. To produce the bank, one can further expand the cell populations. Examples of the characteristic include a subject's name, gender, physical conditions (including genetic disorders and MHC information).

A subject refers to a human or a non-human animal. Examples of a non-human animal include all vertebrates, e.g., mammals, such as non-human primates (particularly higher primates), dogs, rodents (e.g., mice or rats), guinea pigs, cats, farm animals (e.g., horses, cows, sheep, or pigs), and non-mammals, such as birds, amphibians, reptiles, etc. In a preferred embodiment, the subject is a human. In another embodiment, the subject is an experimental animal or animal suitable as a disease model.

The details of one or more embodiments of the invention are set forth in the description below. Other features, objects, and advantages of the invention will be apparent from the description, the drawings, and the claims.

BRIEF DESCRIPTION OF DRAWINGS

FIGS. 2A-2C are flow cytometry histograms showing results of obtaining BLSCs from plasma fractions.

FIG. 13 is photography of RT-PCR results showing expression of GAPDH or beta-actin in SBR and SBT cells, and lack of the expression in BLSC.

DETAILED DESCRIPTION

Figure 1B:
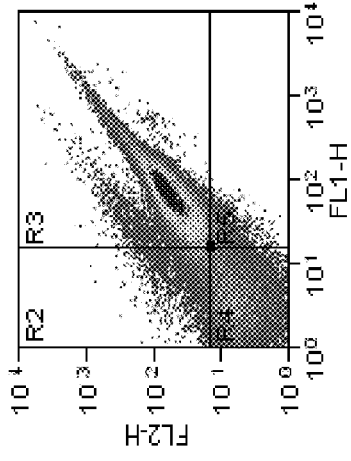
FIGS. 1A-1C are flow cytometry histograms showing results of obtaining BLSCs via hemolysis.

It has been suggested that ES cells can be used to regenerate various cell types (such as neuronal or glial cells in the brain) and thereby treat various degenerative disorders or tissue damage. However, ethical and logistical considerations have hampered the use of ES cells. Stem cells of non-embryonic origins, i.e., post-natal stem cells (e.g., bone marrow-derived mesenchymal stem cells (MSCs)) represent a promising alternative. Nonetheless, this alternative is not always acceptable due to logistical consideration and limited proliferation/differentiation capacity.

This invention relates to a population of stem cells, SBR cells or SBT cells, prepared from non-embryonic origins. Like ES cells, these cells are totipotent or pluripotent. More importantly, they can be obtained at a very high yield and do not develop into teratoma in vivo. They therefore can be used to regenerate differentiated, functional cells in treating various degenerative disorders or tissue damage. As shown in the Example section below, SBR and SBT cells can be easily made, maintained, and expanded in vitro, and induced to differentiation using routine technical approaches. In addition, after grafting the cells into an animal subject (e.g., a mouse), there is no evidence of mitotically active cells, teratomas, or malignant growth. Due to these advantages, the cells represent an alternative to other stem cells.

In a preferred embodiment of this invention, these SBR and SBT cells are prepared from blastomere-like stem cells (BLSC). BLSCs are a population of non-embryonic stem cells in adult or young animals. These cells are totipotent and have the differentiation capability similar to that of embryonic stem cells. See WO2007/100845. Containing a normal chromosomal complement, BLSCs are lineage-uncommitted and can form all somatic (non-reproductive) cells of the body. They can also form the reproductive gametes sperm and/or ovum, and cells and tissues of the embryonic and fetal portions of the placenta. The cells are responsive to lineage-induction agents, proliferation agents, and differentiation inhibitory agents. On the other hand, they are unresponsive to progression agents. Similar to epiblast-like stem cells, BLSCs are not contact inhibited at confluence, but rather form multiple confluent layers of cells as long as they are maintained with an adequate nutrient supply. BLSCs do not express phenotypic expression markers for progenitor or differentiated cells, germ layer lineage stem cells, or epiblast-like stem cells. Instead, they express general and specific embryonic lineage markers, such as the embryonic stem cell markers CD66e, HCEA, CEA, and CEA-CAM-1. BLSCs are normally quiescent in adult tissues. However, when such tissues are injured, BLSCs are activated and differentiate to repair the damaged tissues.

Compared with other stem cells, BLSCs can be obtained from a post-natal tissue with a very high yield. For example, they can be obtained from blood with a yield of more that $2 \times 10^8$/ml blood. On the other hand, as BLSCs are quiescent and do not express genes, their uses for research and therapeutic purposes are limited.

It was unexpected culturing BLSCs with certain chemicals generated totipotent or pluripotent stem cells that express endogenous genes and heterologous genes. Two such totipotent or pluripotent stem cell populations are SBR cells and SBT cells. To obtain SBR cells and SBT cells, one can incubate BLSCs in the presence of RA and TGF-β, respectively.

Figure 1C:
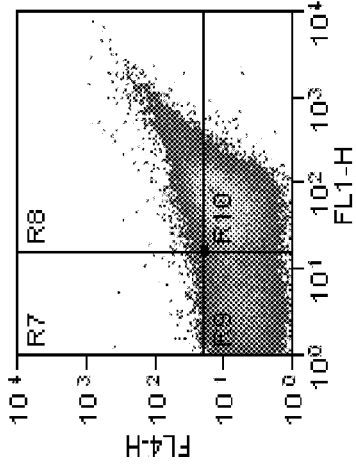
Figure 1A:
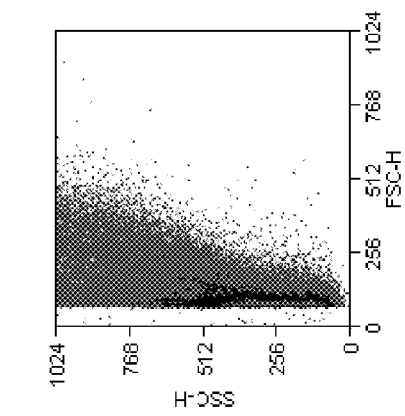
Figure 3C:
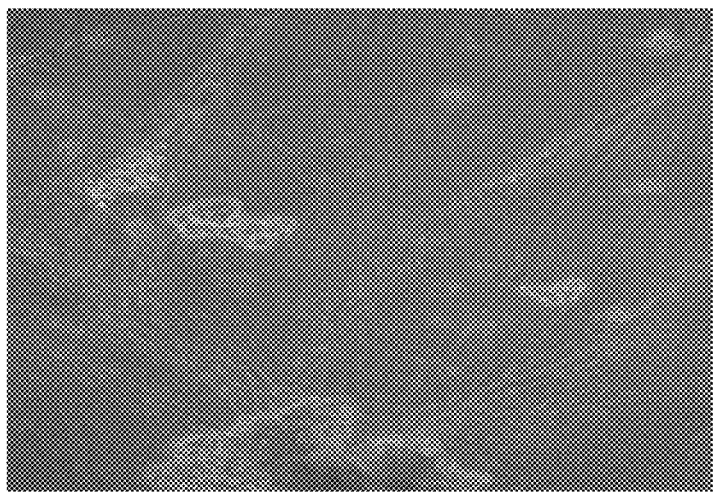
FIGS. 3A-3C are photographs showing cultured BLSCs that form multilayer, mesh net structure.
Figure 3B:
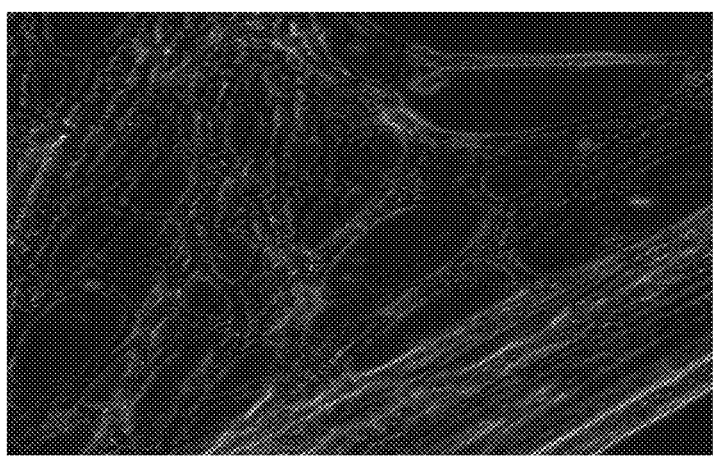
Figure 3A:
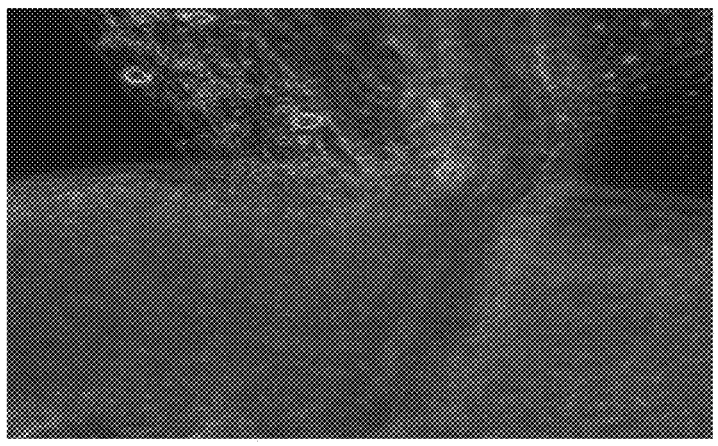
Figure 4:
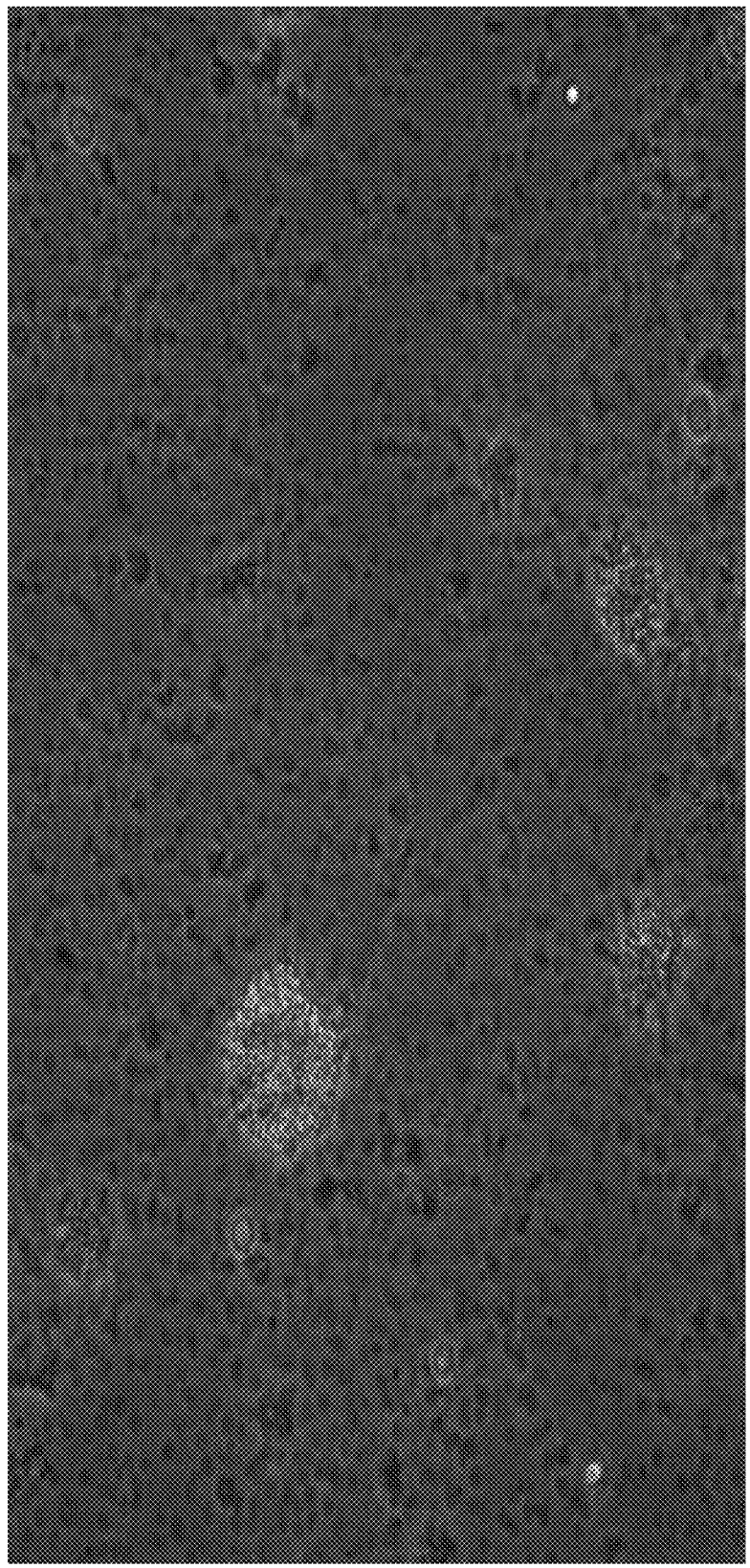
FIG. 4 is a photography showing cultured BLSCs that from aggregations.
Figure 5:
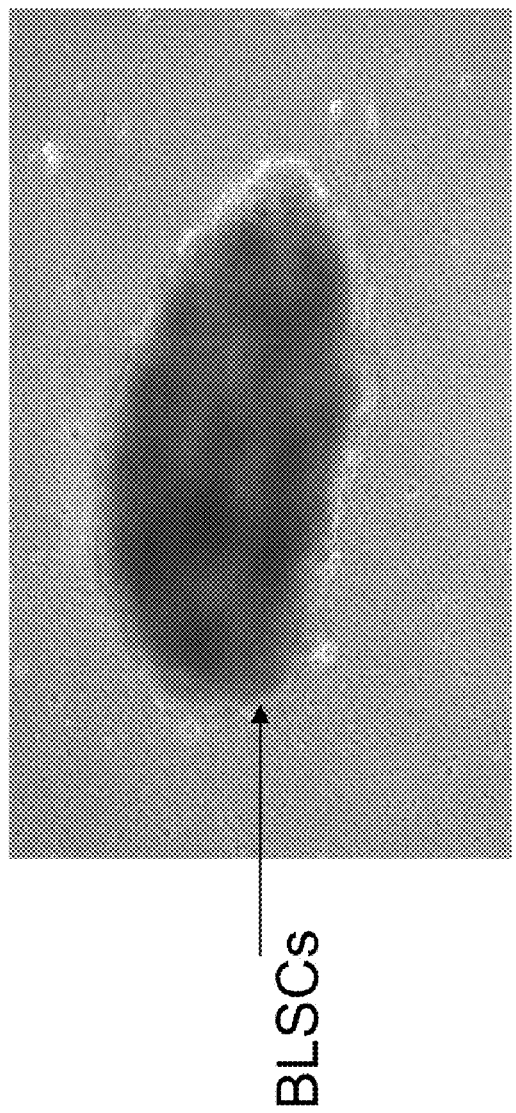
FIG. 5 is a photograph showing cultured BLSCs that from sphere-like cell aggregations.
Figure 6:
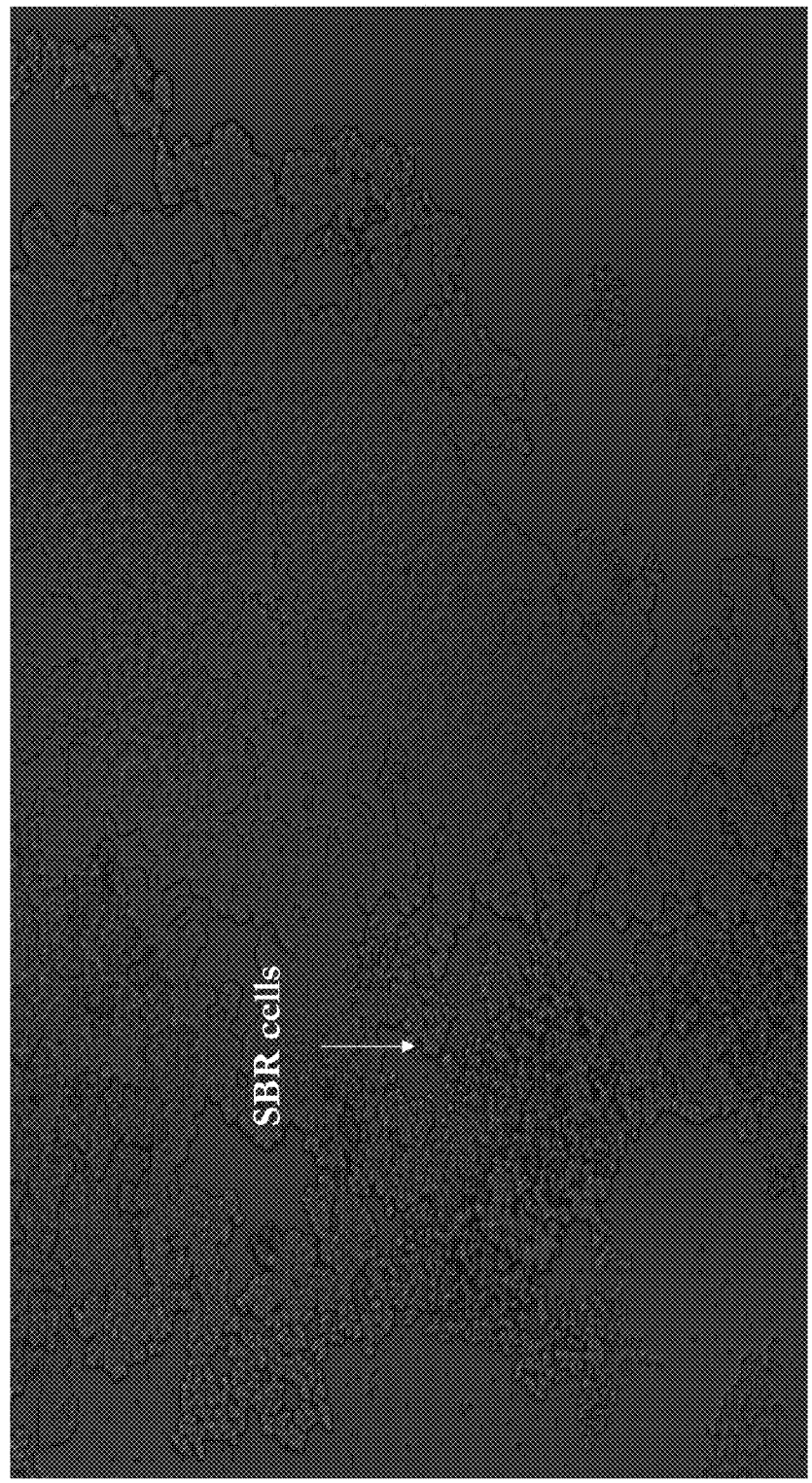
FIGS. 6-8 are photographs showing SBR cells prepared from BLSCs cultured in the presence of retinoic acid.
Figure 7:
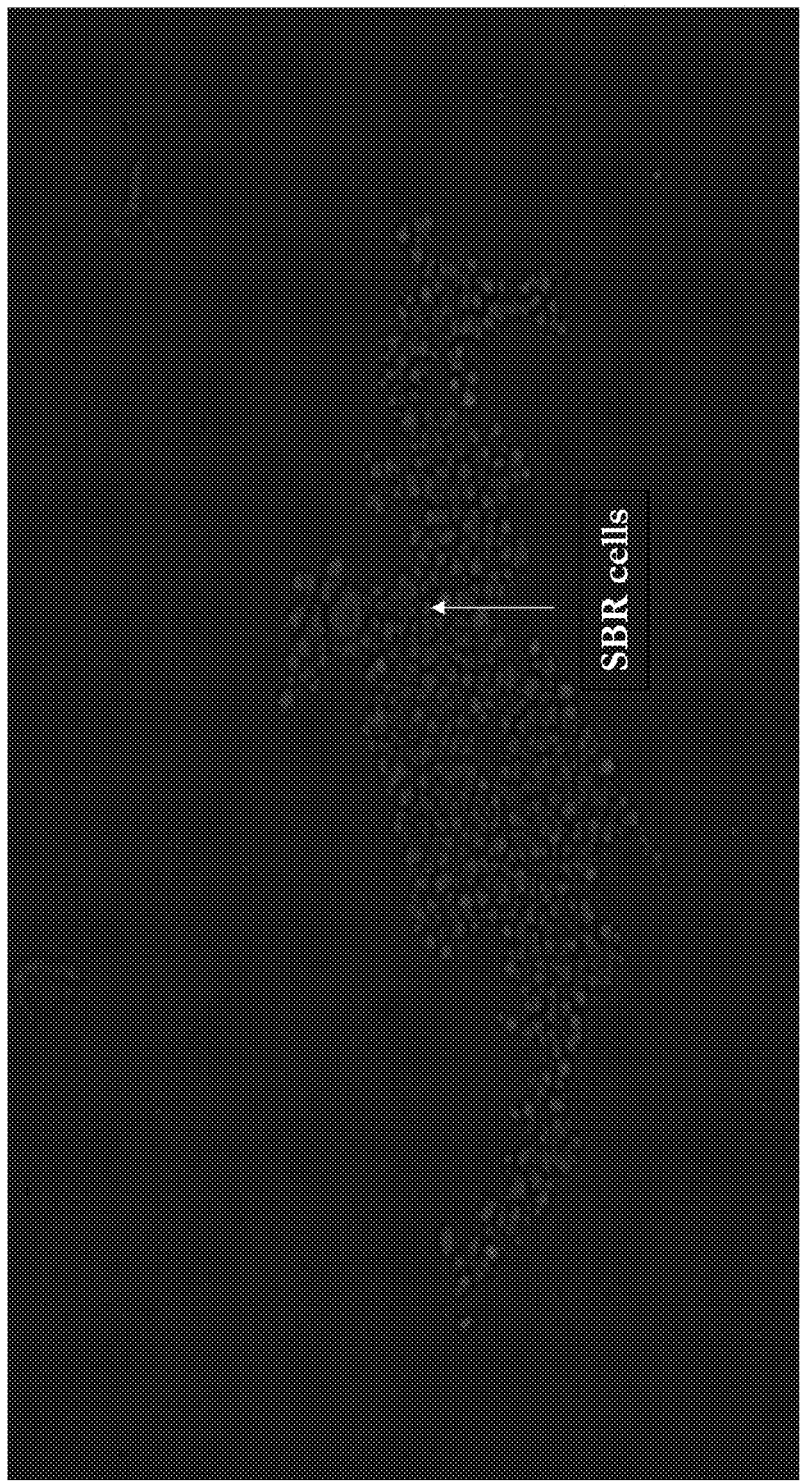
Figure 8:
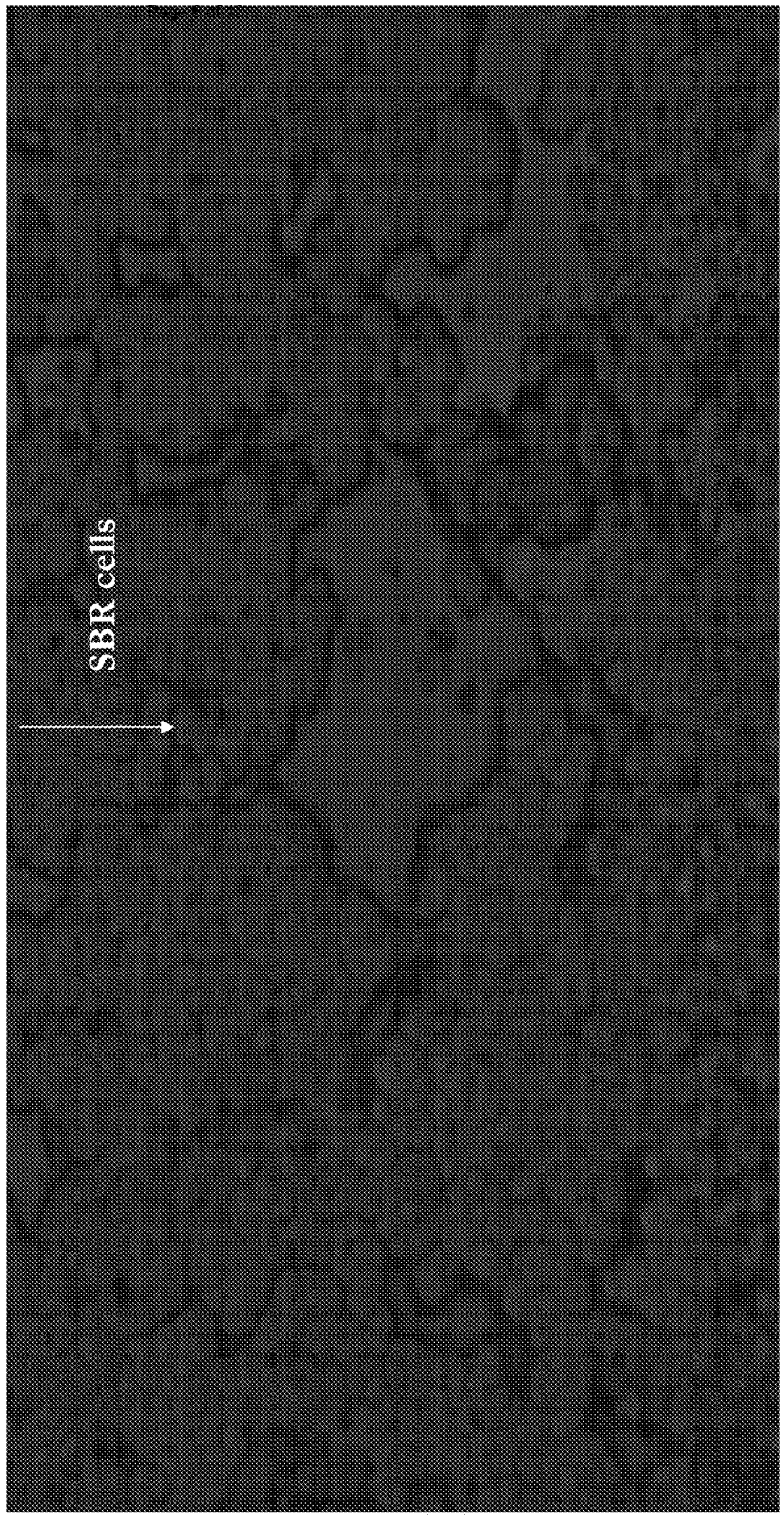
Figure 9:
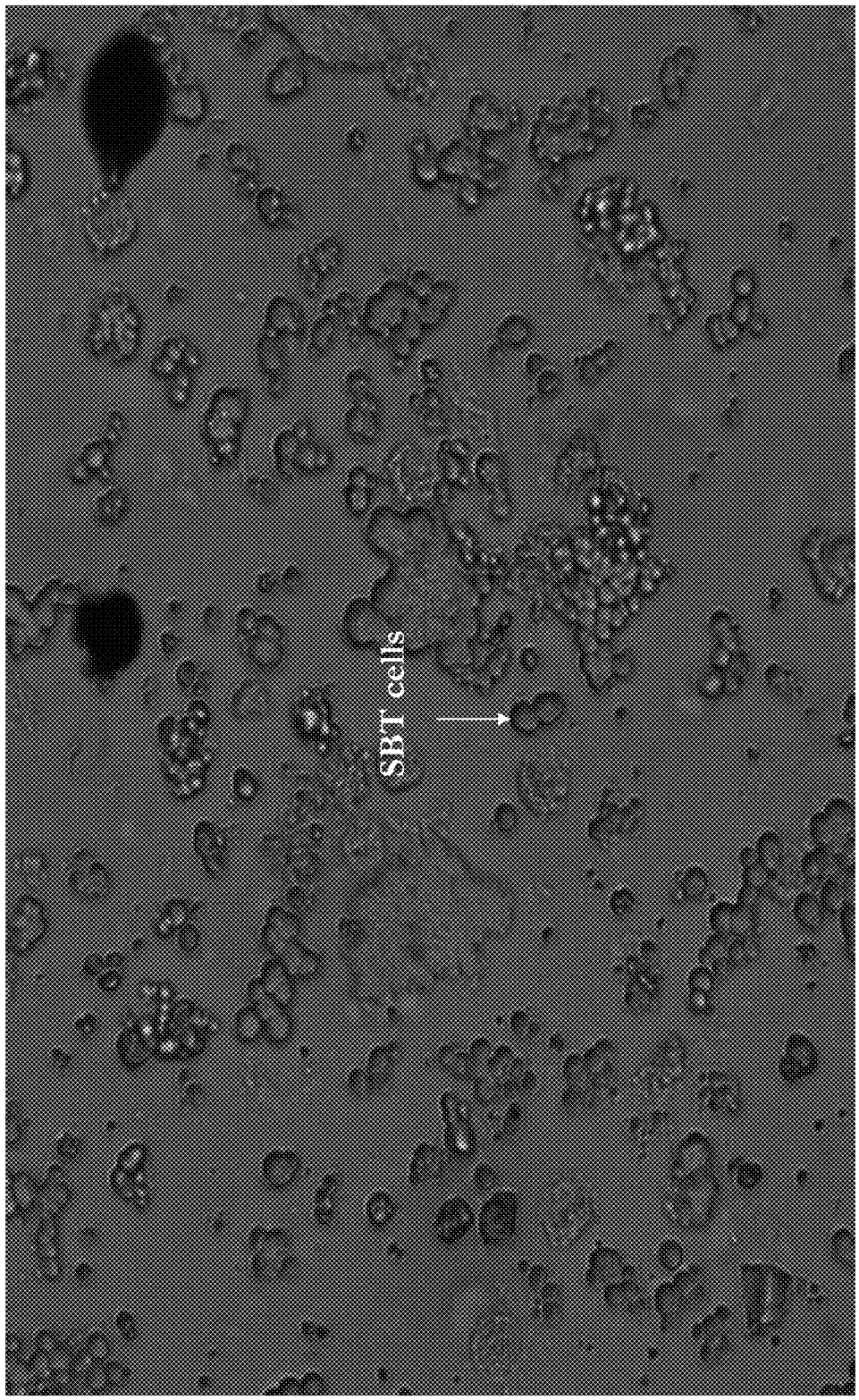
FIGS. 9-12 are photographs showing SBT cells prepared from BLSCs cultured in the presence of TGF-β.
Figure 10:
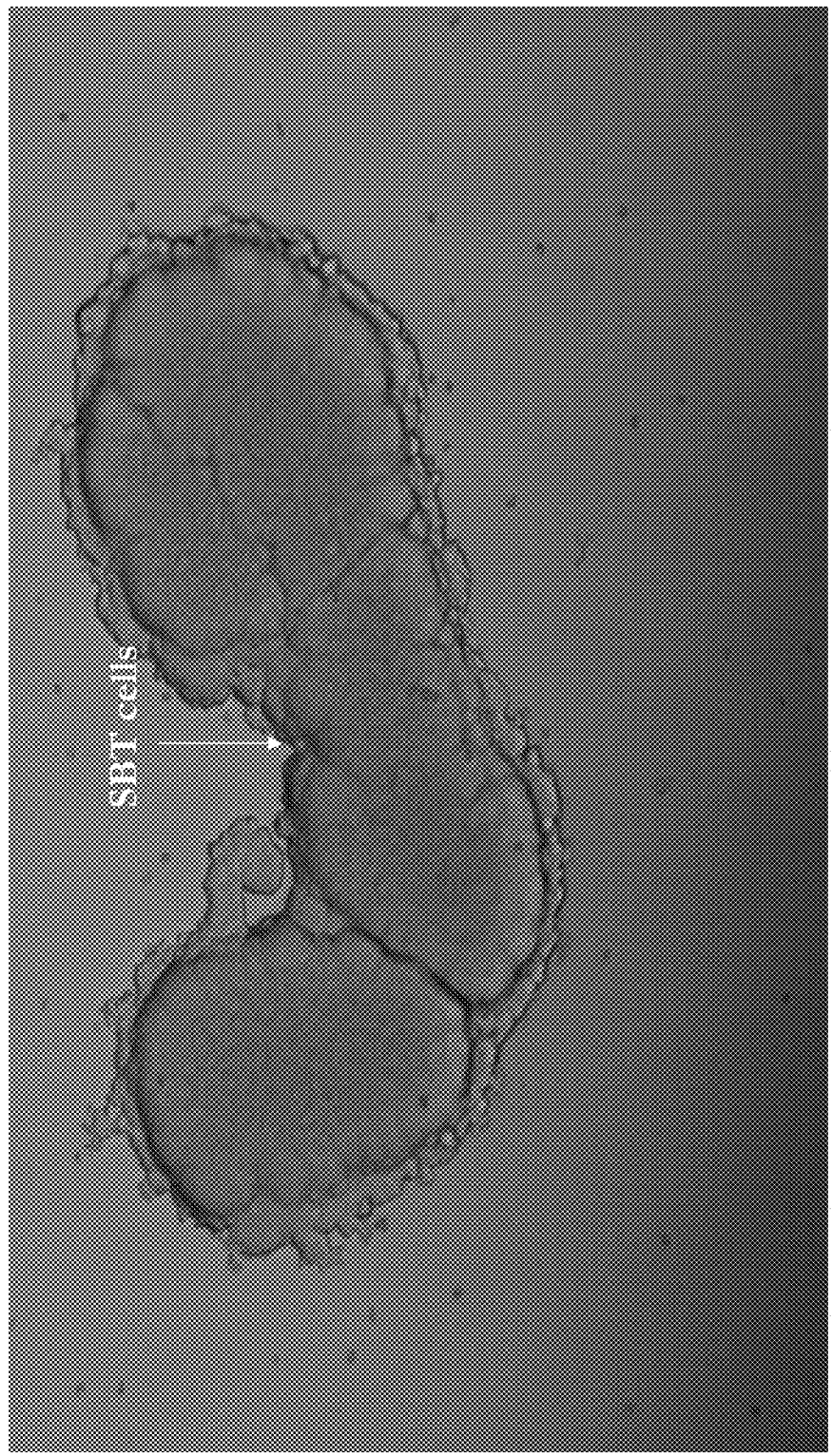
Figure 11:
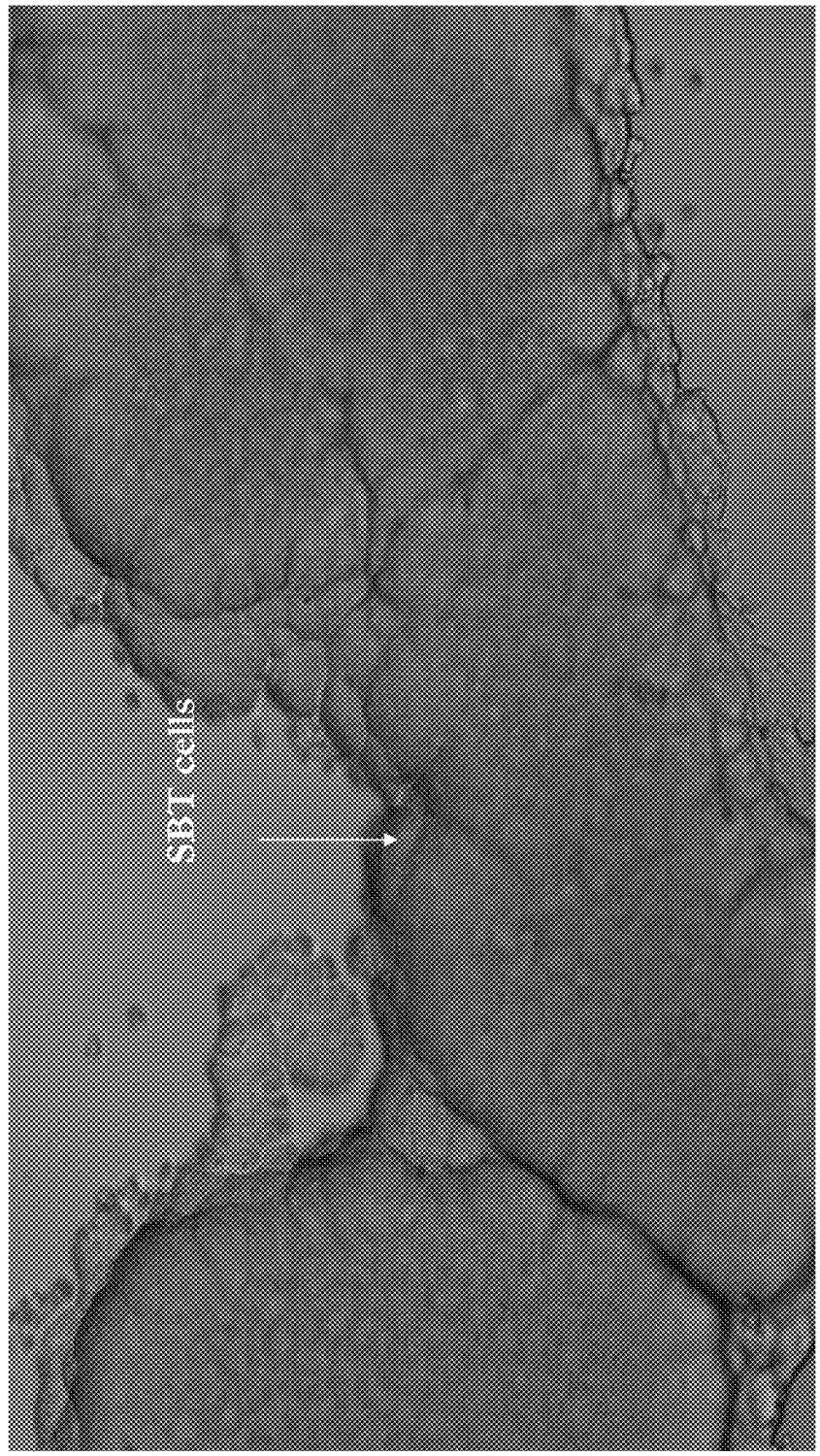
Figure 12:
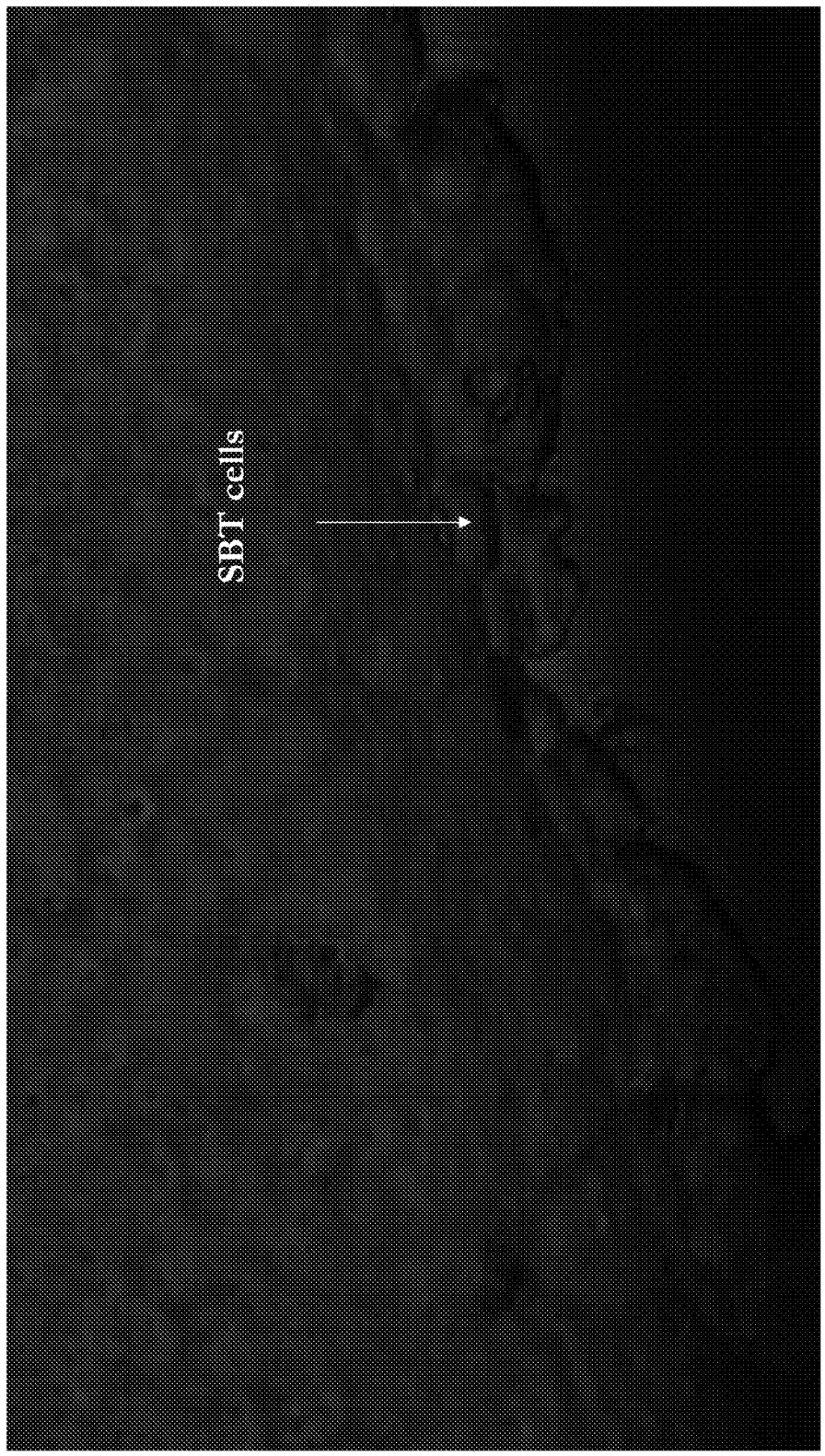

BLSCs can be prepared by the methods described in the Example section below or the method described in WO2007/100845. Generally, the cells can be isolated from many tissues of adult or young animals, including blood, bone marrow, and skeletal muscle. To confirm the cells isolated are indeed BLSC, one can examine a number of characteristics, including (1) sizes of cells in suspension that are less than 1 μm (2) cell surface markers, e.g., CD66e$^+$ and (3) trypan blue staining positive. Antibodies against cell surface markers, such as CD66e can be used. They can be conjugated with suitable labels, such as fluorescein isothiocyanate (FITC), phycoerythrin (PE), or quantum dots. BLSC, which are CD66e$^+$, can be further enriched using flow cytometry (FIGS. 1-2).

The enriched cells are then tested by standard techniques. To confirm the differentiation potential of the cells, they can be induced to form, for example, neuro-glial cells, osteocyte, and adipocyte by methods known in the art. For example, the cells can be passed and cultured to confluence, shifted to an osteogenic medium or an adipogenic medium, and incubated for suitable time (e.g., 3 weeks). The differentiation potential for osteogenesis is assessed by the mineralization of calcium accumulation, which can be visualized by von Kossa staining. To examine adipogenic differentiation, intracellular lipid droplets can be stained by Oil Red O and observed under a microscope. For neural differentiation, the cells can be incubated in a neurogenic medium for suitable duration (e.g., 7 days), and then subjected to serum depletion and incubation of β-mercaptoethanol. After differentiation, cells exhibit the morphology of refractile cell body with extended neuritelike structures arranged into a network. Immunocytochemical stain of lineage specific markers can be further conducted to confirm neural differentiation. Examples of the markers include neuron specific class III β-tubulin (Tuj-1), neurofilament, and GFAP.

Alternatively, to confirm the identity of the isolated cells, one can take advantage of BLSC's lack of contact inhibition. To that end, one can culture the isolated cells to confluence. Under that condition, BLSCs can form sphere-like cell aggregation, multiple confluent layers, or mesh-net structures. In contrast, CD42$^+$ cells cannot form the just-mentioned structure, such as cell aggregation.

The BLSCs thus confirmed can be further propagated in a non-differentiating medium culture for more than 10, 20, 50, or 100 population doublings without indications of spontaneous differentiation, senescence, morphological changes, increased growth rate, or changes in ability to differentiate into neurons. The cells can be stored by standard methods before use.

To prepare SBR cells, one can culture the BLSCs in the presence of 0.1 to 20 μM RA for 2 to 8 weeks. In a prefer embodiment, the BLSCs are cultured in the presence of 1 to 15 μM RA for 2 to 8 weeks, or more preferably, in the presence of 5 to 12 μM RA for 3 to 4 weeks. The pluripotent or totipoent cells thus prepared are 1 to 15 micrometers in size and can form a sheet-like structure in suspension. Any commercial available RA that is suitable for cell culture can be used.

To prepare SBT cells, one can culture the BLSCs in the presence of 1 to 40 nM TGF-β for 2 to 8 weeks. In a prefer embodiment, the BLSCs are cultured in the presence of 2 to 20 nM TGF-β for 2 to 8 weeks, or more preferably, in the presence of 5 to 12 nM TGF-β for 4 to 6 weeks. The pluripotent or totipoent cells are 1 to 15 micrometers in size, have a round shape, and can form aggregation. While any type of TGF-β can be used, highly purified TGF-β is preferred. Examples of TGF-β include mammalian TGF-β (e.g., human TGF-β) or TGF-β having substantially the same biological activity as mammalian TGF-β. Both naturally occurring TGF-β and genetic engineered TGF-β can be used. TGF-β obtained by recombinant DNA technology may be that having the same amino acid sequence as naturally occurring TGF-β or a functionally equivalent thereof. A "functional equivalent" refers to a polypeptide derivative of a naturally occurring TGF-β, e.g., a protein having one or more point mutations, insertions, deletions, truncations, a fusion protein, or a combination thereof. The term "TGF-β" also covers chemically modified TGF-β. Examples of chemically modified TGF-β include TGF-β subjected to conformational change, addition or deletion of the sugar chain, and TGF-β to which a compound such as polyethylene glycol has been bound.

The SBR cells and SBT cells can be confirmed and distinguished from BLSCs according to their sizes, contact inhibition, and trypan blue exclusion (i.e., trypan blue staining negative). BLSCs are smaller (less than 1 micrometer) than SBR cells and SBT cells, and lack contact inhibition or trypan blue exclusion. The SBR cells and SBT cells can also be confirmed according to related cell markers such as $CD10^+$, $CD90^+$, and $CXCR4^+$ by flow cytometric analysis or other standard analysis, such as RT-PCR.

The SBR cells and SBT cells thus prepared can be further tested for their totipotency and pluripotency in the same manner as that for BLSCs described above or other standard techniques known in the art. Under appropriate induction conditions, these cells can differentiate into, e.g., adipocytes, chondrocytes, and cells in the osteogenic lineages in vitro. In addition, these cells are able to differentiate into neuroglial cells under the above-described induction conditions.

The totipotency and pluripotency can be test in vitro. For example, cerebrally ischemic rats receiving intracerebral SBR cells or SBT cells transplantation exhibit significantly improved neurological function than vehicle-treated control rat. The results indicate that intracerebrally administered SBR cells or SBT cells can enter brain, survive, migrate, and improve functional recovery of stroke. In fact, the transplanted cells can differentiate into glial cells (GFAP+), neuron (Nestin+, MAP-2+ and Neu-N+), and vascular endothelial cells (vWF+) to enhance neuroplastic effect in ischemic brain. Cortical neuronal activity as evaluated by Proton MR spectroscopy ($^1$H-MRS) is also much increased on transplantation group in comparison to control. In addition, significantly increased modulation of neurotrophic factor expression in the ischemic hemisphere is also found in the transplantation group.

The SBR cells and SBT cells thus confirmed can be further propagated in a non-differentiating medium culture for more than 10, 20, 50, or 100 population doublings without indications of spontaneous differentiation, senescence, morphological changes, increased growth rate, or changes in ability to differentiate into neurons. The cells can be stored by standard methods before use.

The terms "proliferation" and "expansion" as used interchangeably herein with reference to cells, refer to an increase in the number of cells of the same type by division. The term "differentiation" refers to a developmental process whereby cells become specialized for a particular function, for example, where cells acquire one or more morphological characteristics and/or functions different from that of the initial cell type. The term "differentiation" includes both lineage commitment and terminal differentiation processes. Differentiation may be assessed, for example, by monitoring the presence or absence of lineage markers, using immunohistochemistry or other procedures known to a worker skilled in the art. Differentiated progeny cells derived from progenitor cells may be, but are not necessarily, related to the same germ layer or tissue as the source tissue of the stem cells. For example, neural progenitor cells and muscle progenitor cells can differentiate into hematopoietic cell lineages.

The terms "lineage commitment" and "specification," as used interchangeably herein, refer to the process a stem cell undergoes in which the stem cell gives rise to a progenitor cell committed to forming a particular limited range of differentiated cell types. Committed progenitor cells are often capable of self-renewal or cell division.

The term "terminal differentiation" refers to the final differentiation of a cell into a mature, fully differentiated cell. For example, neural progenitor cells and muscle progenitor cells can differentiate into hematopoietic cell lineages, terminal differentiation of which leads to mature blood cells of a specific cell type. Usually, terminal differentiation is associated with-withdrawal from the cell cycle and cessation of proliferation. The term "progenitor cell," as used herein, refers to a cell that is committed to a particular cell lineage and which gives rise to cells of this lineage by a series of cell divisions. An example of a progenitor cell would be a myoblast, which is capable of differentiation to only one type of cell, but is itself not fully mature or fully differentiated.

1. General Use

The SBR cells and SBT cells of the invention can be used in a variety of ways. One can use the cells for treating degenerative or inherited diseases, avoiding ethical considerations of human embryo manipulation.

To do so, one can isolate BLSCs from a patient, e.g., lacking a functional gene essential for proper development of a tissue or organ. After producing SBR cells and SBT cells from the BLSC, one can introduce into the cells an expression nucleic acid vector encoding a functional version of the gene. The vector can be introduced into the cells via a variety of techniques, including calcium phosphate co-precipitation, DEAE-dextran-mediated transfection, lipofection, electroporation, microinjection, or virus-mediated techniques. Methods not affecting the pluripotency of the cells are preferred. Description of such techniques can be found in, e.g., U.S. Pat. Nos. 7,422,736 and 5,591,625 and US Patent Application NO. 20020127715. After delivering the functional gene into the cells, one can transplant the cells back into the patient using method known in the art. As the cells are produced from the patient, the treatment does not cause immune rejection.

Alternatively, one can make universal donor cells from using SBR cells and SBT cells prepared from a healthy subject. The method for making universal donor cells are known in the art and that for making universal SBR cells and SBT cells will be described below.

Under proper conditions, the transplanted SBR cells and SBT cells can develop into a functional tissue or organ. To facilitate this development, the patient may be administered with factors to induce the development of the cells. Such factors can be small molecule compounds, peptides, and nucleic acids. Examples include, but are not limited to, transforming growth factor β, bone morphogenic proteins, and nerve growth factor.

The SBR cells and SBT cells are also useful for studying development or differentiation mechanisms of lineage development and differentiation. One can identify conditions for inducing the development of totipoent pluripotent stem cells into a specific tissue or organ using such cells as a model system. Further, one can isolate genes that play roles during the development using differential cDNA screening known in the art. See e.g., Shen M. et al., Development, 124:429-42, 1997. One can prepare a cDNA library from the cells that have been induced to develop into a certain lineage, e.g., neuroglial lineage described above. The library can then be used to isolate and study genes differentially expressed. These isolated genes can be further studied to define their roles in respective processes. The related techniques are known in the art. See e.g., U.S. Pat. No. 7,422,736 and US Patent Application No. 20060035373. The SBR cells and SBT cells can also be used to develop into organs or clones of the animals using the methods known in the art. See e.g., Campbell K. et al., Nature, 380: 64-66, 1996. Accordingly, these cells are valuable for the pet and livestock industries, and can be used to preserve endangered animals.

2. Screening Methods

The above-described stem cells can be used in screening assays to identify drugs that can affect a particular cell type in a manner indicating that the drug can be useful for treating a disorder associated with the cell type.

Thus, one aspect of the present invention relates to a method for identifying an agent that alters a function of an undifferentiated SBR cells and SBT cells by contacting the cells with a test agent. A change in a function or gene expression of the cells in presence of the test agent as compared to the function in the absence of the test agent indicates that the test agent is an agent that alters the function of or the gene expression in the cells. The term "test agent" refers to any molecule that is being examined for an ability to alter a function of or gene expression in the cells. Although the method generally is used as a screening assay to identify previously unknown molecules that have a desired activity, the screening methods of the invention also can be used to confirm that an agent known to have a particular activity.

The function can be expression of gene that typically is expressed (or not expressed) in the cells, and the agent can alter the function by increasing or decreasing the level of expression of an expressed gene (e.g., decreasing expression of CD66e), or by turning on the expression of an unexpressed gene (e.g., inducing expression of lineage-specific antigen) in the cells.

In one embodiment, the agent that affects a function of the cells is one that induces differentiation of the cells, thereby producing differentiated cells. Such differentiated cells can be multipotential human stem cells (e.g., hematopoietic stem cells) or can be terminally differentiated cells (e.g., muscle cells, neuronal cells, blood cells, connective tissue, or epithelial cells). As such, the method can be used to identify an agent that induces differentiation of SBR cells and SBT cells to terminally differentiated cells including pancreatic beta cells, hepatocytes, cardiomyocytes, skeletal muscle cells, or any other cell type. Agents or compound thus-identified can be used to treat degenerative disorders, cancer or immune disorders.

The expression level can be determined at either the mRNA level or the protein level. Methods of measuring mRNA levels in a sample are well known in the art. To measure mRNA levels, cells can be lysed and the levels of mRNA in the lysates, whether purified or not, can be determined by, e.g., hybridization assays (using detectably labeled gene-specific DNA or RNA probes) and quantitative or semi-quantitative RT-PCR (using appropriate gene-specific primers). Alternatively, quantitative or semi-quantitative in situ hybridization assays can be carried out on tissue sections or unlysed cell suspensions using detectably (e.g., fluorescent or enzyme) labeled DNA or RNA probes. Additional mRNA-quantifying methods include the RNA protection assay (RPA) method and the serial analysis of gene expression (SAGE) method, as well as array-based technologies.

Methods of measuring protein levels in a sample are also well known in the art. Some of them employ antibodies (e.g., monoclonal or polyclonal antibodies) that bind specifically to a target protein. In such assays, the antibody itself or a secondary antibody that binds to it can be detectably labeled. Alternatively, the antibody can be conjugated with biotin. Its presence can be determined by detectably labeled avidin (a polypeptide that binds to biotin). Combinations of these approaches (including "multi-layer sandwich" assays) can be used to enhance the sensitivity of the methodologies. Some protein-measuring assays (e.g., ELISA or Western blot) can be applied to body fluids or to lysates of cells, and others (e.g., immunohistological methods or fluorescence flow cytometry) can be applied to histological sections or unlysed cell suspensions. Appropriate labels include radionuclides (e.g., $^{125}I$, $^{131}I$, $^{35}S$, $^{3}H$, or $^{32}P$), enzymes (e.g., alkaline phosphatase, horseradish peroxidase, luciferase, or β-glactosidase), fluorescent/luminescent agents (e.g., fluorescein, rhodamine, phycoerythrin, GFP, BFP, and Qdot™ nanoparticles supplied by the Quantum Dot Corporation, Palo Alto, Calif.). Other applicable methods include quantitative immunoprecipitation or complement fixation assays.

A test agent can be any type of molecule, for example, a polynucleotide, a peptide, a peptidomimetic, peptoids such as vinylogous peptoids, a small organic molecule, or the like, and can act in any of various ways to alter a function of SBR cells and SBT cells. For example, the test agent can act extracellularly by binding to a cell surface receptor expressed by the cells, thereby altering a function mediated by binding of a ligand that generally binds to and acts via the receptor. Alternatively, the test agent can be one that traverses the cell membrane, either passively or via an active transport mechanism, and acts within the cells to alter a function.

A peptide test agent can be any polymer of amino acids or amino acid analogs, and can vary from about three to four residues to hundreds or thousands. Peptide test agents can be prepared by chemical synthesis, or using methods of protein purification, followed by proteolysis and, if desired, further purification by chromatographic or electrophoretic methods, or can be expressed from an encoding polynucleotide. A peptide test agent can be based on a known peptide, for example, a naturally occurring peptide, but can vary from the naturally occurring sequence, for example, by containing one or more amino acid analogs.

A polynucleotide agent can be a sequence of two or more deoxyribonucleotides or ribonucleotides that are linked together by a phosphodiester bond. It can be RNA or DNA, which can be a gene or a portion thereof, a cDNA, an RNAi agent, a synthetic polydeoxy-ribonucleic acid sequence, or the like, and can be single stranded or double stranded, as well as a DNA/RNA hybrid. It can be a naturally occurring nucleic acid molecule, which can be isolated from a cell, as well as a synthetic molecule, which can be prepared, for example, by methods of chemical synthesis or by enzymatic methods such as by the polymerase chain reaction (PCR). In various embodiments, a polynucleotide of the invention can contain nucleoside or nucleotide analogs, or a backbone bond other than a phosphodiester bond. Such nucleotide analogs are well known in the art and commercially available, as are polynucleotides containing such nucleotide analogs (Lin et al., Nucl. Acids Res. 22:5220-5234, 1994; Jellinek et al., Biochemistry 34:11363-11372, 1995; Pagratis et al., Nature Biotechnol. 15:68-73, 1997).

A polynucleotide test agent can be contacted with or introduced into SBR cells and SBT cells using methods as disclosed herein or otherwise known in the art. Generally, but not necessarily, the polynucleotide is introduced into the cell, where it effects its function either directly, or following transcription or translation or both. For example, the polynucleotide can encode a peptide test agent, which is expressed in the cells and alters a function of the cells. A polynucleotide test agent also can be, or can encode, an antisense molecule, a ribozyme or a triplexing agent, which can be designed to target one or more specific target nucleic acid molecules.

Candidate agents or compounds to be screened (e.g., proteins, peptides, peptidomimetics, peptoids, antibodies, small molecules, or other drugs) can be obtained using any of the numerous approaches in combinatorial library methods known in the art. Such libraries include: peptide libraries, peptoid libraries (libraries of molecules having the functionalities of peptides, but with a novel, non-peptide backbone that is resistant to enzymatic degradation); spatially addressable parallel solid phase or solution phase libraries; synthetic libraries obtained by deconvolution or affinity chromatography selection; and the "one-bead one-compound" libraries. See, e.g., Zuckermann et al. 1994, J. Med. Chem. 37:2678-2685; and Lam, 1997, Anticancer Drug Des. 12:145. Examples of methods for the synthesis of molecular libraries can be found in, e.g., DeWitt et al., 1993, PNAS USA 90:6909; Erb et al., 1994, PNAS USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994 J. Med. Chem. 37:1233. Libraries of compounds may be presented in solution (e.g., Houghten, 1992, Biotechniques 13:412-421), or on beads (Lam, 1991, Nature 354:82-84), chips (Fodor, 1993, Nature 364:555-556), bacteria (U.S. Pat. No. 5,223,409), spores (U.S. Pat. No. 5,223,409), plasmids (Cull et al., 1992, PNAS USA 89:1865-1869), or phages (Scott and Smith 1990, Science 249:386-390; Devlin, 1990, Science 249:404-406; Cwirla et al., 1990, PNAS USA 87:6378-6382; Felici 1991, J. Mol. Biol. 222:301-310; and U.S. Pat. No. 5,223,409).

3. Treating Degenerative Disorders

Within the scope of this invention is a method of treating a degenerative disease, alleviating the symptom of the disorder, or delaying the onset of the disorder in a subject. A subject to be treated can be identified by standard techniques for diagnosing the conditions or disorders of interest. The treatment method entails administering to a subject in need thereof an effective amount of the above-described SBR cells or SBT cells.

A degenerative disease refers to a disorder where the function or structure of an affected tissue or organ progressively deteriorate over time, whether due to genetic defects, injury, lack of proper cell differentiation (e.g., that in cell proliferative disorders), normal bodily wear, or lifestyle choices. Examples of degenerative diseases include neurodegenerative diseases (e.g., Alzheimer's disease, Parkinson disease, Huntington's disease, multiple sclerosis, and amyotrophic lateral sclerosis (ALS)), other nervous system disorders (including transverse myelitis, demyelination occurring after trauma to the brain or spinal cord, acute brain injury, head trauma, spinal cord injury, peripheral nerve injury, ischaemic brain injury, hereditary myelin disorder of the CNS, epilepsy, perinatal asphyxia, asphyxia, anoxia, status epilepticus, Shy-Drager syndrome, autism, and stroke), cancer or a condition resulting from related cancers therapy (e.g., chemotherapy); metabolic disorders (e.g., diabetes/diabetes mellitus. Niemann Pick disease); autoimmune or inflammation related disorders (e.g., erythematosis, inflammatory bowel disease (IBD), postatitis, osteoarthritis, osteoporosis, rheumatoid arthritis, lupus, diabetes, and asthma), ocular disorders (such as glaucoma, retinitis pigmentosa, Norrie disease, and macular degeneration); heart and circulatory disorders (e.g., atherosclerosis, heart failure myocardial infarction, and cardiovascular disease); blood disorders such as Wiscott Aldrich syndrome; muscular dystrophy; gastrointestinal disease; kidney disease; liver disease; lung disease, adrenal disorders (such as Addison's disease), a condition resulting from an injury such as a burn or a stroke, including damaged tissue (such as flesh wounds, age damaged cells and age damaged tissue), a condition associated with aging (e.g., hair loss, including male pattern baldness and alopecia areata), viral conditions (such as hepatitis C infection and acquired immune deficiency disorder), and any other disorder that an organ transplant or stem cells can be used to restore, regenerate, or otherwise ameliorate signs and/or symptoms associated with the disorder. The method of this invention can be used in treating erectile dysfunction and in plastic surgery or breast implantation for female.

4. Treating Parkinson Disease and Other Neurodegenerative Diseases

Within the scope of this invention is a method of treating brain or CNS tissue damage or alleviate the symptom of the disorder in a subject. The method includes identifying a subject suffering from or being at risk for developing brain tissue damage. The subject can be a human or a non-human mammal, such as a cat, a dog, or a horse. Examples of the brain tissue damage include those caused by a cerebral ischemia (e.g., chronic stroke) or a neurodegenerative disease (e.g., Parkinson's disease, Alzheimer's disease, Spinocerebellar disease, or Huntington's disease). A subject to be treated can be identified by standard techniques for diagnosing the conditions or disorders of interest. The treatment method entails administering to a subject in need thereof an effective amount of the above-described SBR cells or SBT cells or active agents/compounds.

The therapeutic effects of the cells can be accessed according to standard methods. For example, to confirm efficacy in promoting cerebrovascular angiogenesis, one can examine the subject before and after the treatment by standard brain imaging techniques, such as computed tomography (CT), Doppler ultrasound imaging (DUI), magnetic resonance imaging (MRI), and proton magnetic resonance spectroscopy ($^1$H-MRS). For example, $^1$H-MRS represents a non-invasive means to obtain biochemical information correlated to brain metabolic activity (Lu et al., 1997, Magn. Reson. Med. 37, 18-23). This technique can be applied to evaluate the metabolic changes involved in cerebral ischemia with or without stem cell transplantation. For example, it can be used to study the N-acetylaspartate (NAA) concentration in the brain, a marker of neuronal integrity. Although NAA redistribution and trapping in neuronal debris limits its use as a quantitative neuronal marker, decreases in brain NAA concentration in cerebral ischemia can be considered as an index of neuronal loss or dysfunction (Demougeot et al., 2004, J. Neurochem. 90, 776-83). Therefore, an NAA level, measured by $^1$H-MRS, is a useful indicator for following the effect of stem cell transplantation after cerebral ischemia.

5. Cancer

The above-described SBR cells or SBT cells can also be used to treat cancer and other cellular proliferative disorders. A cellular proliferative disorder refers to a disorder characterized by uncontrolled, autonomous cell growth (including malignant and non-malignant growth). The term "cancer" refers to class of diseases that are characterized by uncontrolled cell growth, invasion, and sometimes metastasis. Cancer cells have the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type, or stage of invasiveness. Examples of cancer include, but are not limited to, carcinoma and sarcoma such as leukemia, sarcoma, osteosarcoma, lymphomas, melanoma, glioma, pheochromocytoma, hepatoma, ovarian cancer, skin cancer, testicular cancer, gastric cancer, pancreatic cancer, renal cancer, breast cancer, prostate cancer, colorectal cancer, cancer of head and neck, brain cancer, esophageal cancer, bladder cancer, adrenal cortical cancer, lung cancer, bronchus cancer, endometrial cancer, nasopharyngeal cancer, cervical or liver cancer, and cancer of unknown primary site.

6. Gene Therapy

The above-descried cells and methods can be used in various gene therapy methods known in the art. Gene therapy includes both ex vivo and in vivo techniques. Specifically, the above-described stem cells can be genetically engineered ex vivo with an oligonucleotide modulator or a nucleic acid molecule encoding the modulator, with the engineered cells then being provided to a patient to be treated. Cell cultures may be formulated for administration to a patient, for example, by dissociating the cells (e.g., by mechanical dissociation) and intimately admixing the cell with a pharmaceutically acceptable carrier (e.g., phosphate buffered saline solution). Alternatively, cells may be cultured on a suitable biocompatible support and transplanted into a patient. The engineered cells are typically autologous so as to circumvent xenogeneic or allotypic rejection. Such ex vivo methods are well known in the art.

The cells can be engineered by administration of the oligonucleotide or nucleic acid molecule using techniques known in the art. For example, oligonucleotides and other nucleic acid molecules can be administered by direct injection of a "naked" nucleic acid molecule (Felgner and Rhodes, (1991) Nature 349:351-352; U.S. Pat. No. 5,679,647) or a nucleic acid molecule formulated in a composition with one or more other agents which facilitate uptake of the nucleic acid molecule by the cell, such as saponins (see, for example, U.S. Pat. No. 5,739,118) or cationic polyamines (see, for example, U.S. Pat. No. 5,837,533); by microparticle bombardment (for example, through use of a "gene gun"; Biolistic, Dupont); by coating the nucleic acid molecule with lipids, cell-surface receptors or transfecting agents; by encapsulation of the nucleic acid molecule in liposomes, microparticles, or microcapsules; by administration of the nucleic acid molecule linked to a peptide which is known to enter the nucleus; or by administration of the nucleic acid molecule linked to a ligand subject to receptor-mediated endocytosis, which can be used to target cell types specifically expressing the receptors.

A nucleic acid-ligand complex can be formed in which the ligand comprises a fusogenic viral peptide to disrupt endosomes, allowing the nucleic acid to avoid lysosomal degradation; or the nucleic acid molecule can be targeted for cell specific uptake and expression in vivo by targeting a specific receptor. In addition, an efficient method for the introduction, expression and accumulation of antisense oligonucleotides in the cell nucleus is described in U.S. Pat. No. 6,265,167, which allows the antisense oligonucleotide to hybridise to the sense mRNA in the nucleus, and thereby prevents the antisense oligonucleotide being either processed or transported into the cytoplasm. The present invention also contemplates the intracellular introduction of the nucleic acid molecule and -subsequent incorporation within host cell DNA for expression by homologous recombination known in the art.

The polynucleotide can also be incorporated into a suitable expression vector. A number of vectors suitable for gene therapy applications are known in the art (see, for example, Viral Vectors: Basic Science and Gene Therapy, Eaton Publishing Co. (2000)).

The expression vector may be a plasmid vector. Methods of generating and purifying plasmid DNA are rapid and straightforward. In addition, plasmid DNA typically does not integrate into the genome of the host cell, but is maintained in an episomal location as a discrete entity eliminating genotoxicity issues that chromosomal integration may raise. A variety of plasmids are now readily available commercially and include those derived from *Escherichia coli* and *Bacillus subtilis*, with many being designed particularly for use in mammalian systems. Examples of plasmids that may be used in the present invention include, but are not limited to, the eukaryotic expression vectors pRc/CMV (Invitrogen), pCR2.1 (Invitrogen), pAd/CMV and pAd/TR5/GFPq (Massie et al., (1998) Cytotechnology 28:53-64). In an exemplary embodiment, the plasmid is pRc/CMV, pRc/CMV2 (Invitrogen), pAdCMV5 (IRB-NRC), pcDNA3 (Invitrogen), pAdMLP5 (IRB-NRC), or PVAX Invitrogen).

The expression vector can be a viral-based vector. Examples of viral-based vectors include, but are not limited to, those derived from replication deficient retrovirus, lentivirus, adenovirus and adeno-associated virus. Retrovirus vectors and adeno-associated virus vectors are currently the recombinant gene delivery system of choice for the transfer of exogenous oligonucleotides or genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. Retroviruses, from which retroviral vectors may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumour virus. Specific retroviruses include pLG, pZIP, pWE and pEM, which are well known to those skilled in the art.

7. Cell Banking

The invention features a stem cell bank or library for a convenient systematic access to different stem cell lines. Stem cells in the bank or library are derived from the above-described BLSC, SBR cells, or SBT cells, which are from healthy subjects or subjects having known disease states or disease symptoms would be invaluable to users, e.g., researchers. Also with the scope of the invention is a cell bank or library having cells differentiated from the above-described stem cells. Examples of cells differentiated from the stem cells include brain cells, neurons, astrocytes, glial cells, T cells, B cells, cartilage cells, bone cells, pancreatic islet cells, fat cells, heart cells, liver cells, kidney cells, lung cells, muscle cells, and eye cells. The subjects may be human or nonhuman vertebrates. The stem cells can be derived from any mammalian organism, such as human, mouse, rabbits, cows, pigs, and the like.

The cells in the bank or library are catalogued according to predetermined characteristics, including phenotypic information, morphological characteristics, differentiation profile, blood type, major histocompatibility complex, disease state of donor, or genotypic information (e.g. single nucleated polymorphisms (SNPs) of a specific nucleic acid sequence associated with a gene, or genomic or mitochondrial DNA). The cells are stored under appropriate conditions (typically by freezing) to keep the stem cells alive and functioning. Cataloguing may constitute creating a centralized record of the characteristics obtained for each cell population, such as, but not limited to, an assembled written record or a computer database with information inputted therein. Essentially, this embodiment pertains to the production of a stem cell bank. The stem cell bank facilitates the selection from a plurality of samples of a specific stem cell sample suitable for a user's needs. Thus, another embodiment of the subject invention pertains to a stem cell bank comprising a plurality of stem cells samples obtained from separate sources and which are characterized and catalogued according to at least one predetermined characteristic. An additional embodiment pertains to a method of establishing a stem cell bank comprising collecting stem samples from multiple sources; cataloguing the samples according to at least one predetermined characteristic and storing the cells under conditions that keep cells viable.

With the scope of this invention is a stem cell banking system containing a plurality of stem cell populations disposed in individual containers under conditions to keep the stem cell populations viable; a database computer comprising at least one processing module, a display, and a storage medium comprising information of at least one characteristic for each of the stem cell population; and at least one program code module for causing the information to be viewable on said display upon command by a user. In a specific embodiment, the invention features a stem cell banking system where the stem cell populations have stem cells obtained from subjects who have a disease condition. The disease condition may include the above-described degenerative diseases. Stem cells are harvested from different subjects having a different disease, and the stem cells are characterized. The characteristic(s) is/are inputted into the database computer. In addition, or alternatively, cells are characterized based on a specific phenotype not necessarily associated with a disease condition. For example, liver cells can be characterized based on their ability to metabolize certain compounds such as caffeine, alcohol, drug agents, etc. to study genetic bases of such different metabolism abilities, or underlying physiology associated therewith. Other types of cells can be characterized based on functional and/or morphological phenotypes.

In certain embodiments, cells differentiated from the SBR cells or SBT cells may be subjected to conditions to influence differentiation or dedifferentiation through introduction of engineered vectors, or other genetic material. Dedifferentiation comprises the manipulation of a cell such that it takes on the properties of a less differentiated cell.

The stem cell libraries of the invention can be used to screen for agents or compounds that may be used to treat degenerative disorders, cancer or immune disorders in the manner described above. The libraries are suitable for high throughput screening and are useful for identifying agents that are specifically effective for a particular subject. For a high throughput screening, the stem cells can be introduced into wells of a multiwell plate or of a glass slide or microchip, and can be contacted with the test agent. Generally, the cells are organized in an array, particularly an addressable array, such that robotics conveniently can be used for manipulating the cells and solutions and for monitoring the cells, particularly with respect to the function being examined. An advantage of using a high throughput format is that a number of test agents can be examined in parallel, and, if desired, control reactions also can be run under identical conditions as the test conditions. As such, the screening methods of the invention provide a means to screen one, a few, or a large number of test agents in order to identify an agent that can alter a function of the stem cells, for example, an agent that induces the cells to differentiate into a desired cell type, or that prevents spontaneous differentiation, for example, by maintaining a high level of expression of regulatory molecules.

8. Universal Donor Cells

The above-described stem cells can be genetically engineered to generate histocompatible donor cells or tissues for transplantation. The goal of transplantation and cell therapy is to successfully replace failing tissues or organs with functional donor tissues or organs. However, for transplantation to succeed, two major barriers need to be overcome: the availability of suitable donor tissues or organs and immune rejection. The replacement of failing tissues or organs and the treatment of the rejection is restricted by the limited number of acceptable donors and the need for co-administration of toxic immuno-suppressive drugs in conjunction with long term immuno-suppressive protocols. Current and experimental transplantation protocols rely mainly on sibling donors, other small pools of allogeneic donors, and xenogeneic donors. The above-described genetically engineered stem cells can be used to overcome these limitations.

More specifically, the stem cells descried herein can be genetically engineered to not express on their surface class II MHC molecules. More preferably, the cells are engineered to not express substantially all cell surface class I and class II MHC molecules. As used herein, the term "not express" mean either that an insufficient amount is expressed on the surface of the cell to elicit a response or that the protein that is expressed is deficient and therefore does not elicit a response.

The MHC molecules refer to HLA molecules, specifically of classes HLA A, B and C, and class II HLA DP, DQ, and DR, and their subclasses. This terminology is generally construed as specific to the human MHC, but is intended herein to include the equivalent MHC genes from the donor cell species, for example, if the cells are of porcine origin, the term HLA would refer to the equivalent porcine MHC molecules, whether MHC I or II. When the class II MHC molecules are removed, CD4+ T-cells do not recognize the genetically engineered endothelial cells; when both the class I and class II MHC molecules are removed neither CD4+ nor CD8+ cells recognize the modified cells.

The preferred genetic modification performed on the stem cells includes 1) disrupting the endogenous invariant chain gene which functions in the assembly and transport of class II MHC molecules to the cell surface and loading of antigenic peptide, and 2) disrupting the endogenous $\beta_2$-microglobulin gene ($\beta_2$M gene) which codes for a protein required for the cell surface expression of all class I MHC molecules. Alternatively, just the invariant chain gene is disrupted. Invariant chain is believed to be required for the insertion of antigienic peptide fragments into the MHC class II molecule. Together, the antigenic peptide and MHC is recognized by T cells. In the absence of antigenic peptide, T cell recognition is not normally obtained, nor is the MHC class II molecule folded properly. Thus, in cells lacking invariant chain, presentation of peptide will be abrogated and even if minuscule amounts of cell surface MHC are obtained, they may be devoid of peptide and therefore, non-immunogenic.

Disruption of these genes can be accomplished by means of homologous recombination gene targeting techniques. These techniques are well known in the art. See U.S. Pat. Nos. 6,916,654 and 6,986,887, Zijlstra et al., 1989, Nature 342: 435438; and Koller et al., 1990 Science 248:1227-1230.

9. Compositions

The present invention provides for pharmaceutical compositions containing the above-descried cells or active agents/compounds. Pharmaceutical compositions can be prepared by mixing a therapeutically effective amount of the cells or active agents/compounds, and, optionally other active substance, with a pharmaceutically acceptable carrier. The carrier can have different forms, depending on the route of administration. Examples of other active substance include active compounds known or identified by the screening method of described above.

The above-described pharmaceutical compositions can be prepared by using conventional pharmaceutical excipients and methods of preparation. All excipients may be mixed with disintegrating agents, solvents, granulating agents, moisturizers, and binders. As used herein, the term "effective amount" or 'therapeutically effective amount' refers to an amount which results in measurable amelioration of at least one symptom or parameter of a specific disorder. A therapeutically effective amount of the above-descried cells can be determined by methods known in the art. An effective amount for treating a disorder can easily be determined by empirical methods known to those of ordinary skill in the art. The exact amount to be administered to a patient will vary depending on the state and severity of the disorder and the physical condition of the patient. A measurable amelioration of any symptom or parameter can be determined by a person skilled in the art or reported by the patient to the physician. It will be understood that any clinically or statistically significant attenuation or amelioration of any symptom or parameter of the above-described disorders is within the scope of the invention. Clinically significant attenuation or amelioration means perceptible to the patient and/or to the physician.

The phrase "pharmaceutically acceptable" refers to molecular entities and other ingredients of such compositions that are physiologically tolerable and do not typically produce unwanted reactions when administered to a human. Preferably, the term "pharmaceutically acceptable" means approved by a regulatory agency of the federal or a state government or listed in the U.S. Pharmacopeia or other generally recognized pharmacopeia for use in mammals, and more particularly in humans. Pharmaceutically acceptable salts, esters, amides, and prodrugs refers to those salts (e.g., carboxylate salts, amino acid addition salts), esters, amides, and prodrugs which are, within the scope of sound medical judgment, suitable for use in contact with the tissues of patients without undue toxicity, irritation, allergic response, and the like, commensurate with a reasonable benefit/risk ratio, and effective for their intended use.

A carrier applied to the pharmaceutical compositions described above refers to a diluent, excipient, or vehicle with which a compound is administered. Such pharmaceutical carriers can be sterile liquids, such as water and oils. Water or aqueous solution, saline solutions, and aqueous dextrose and glycerol solutions are preferably employed as carriers, particularly for injectable solutions. Suitable pharmaceutical carriers are described in "Remington's Pharmaceutical Sciences" by E. W. Martin, 18th Edition.

The above-descried cells can be administered to individuals through infusion or injection (for example, intravenous, intrathecal, intramuscular, intraluminal, intratracheal, intraperitoneal, or subcutaneous), orally, transdermally, or other methods known in the art. Administration may be once every two weeks, once a week, or more often, but frequency may be decreased during a maintenance phase of the disease or disorder.

Both heterologous and autologous cells can be used. In the former case, HLA-matching should be conducted to avoid or minimize host reactions. In the latter case, autologous cells are enriched and purified from a subject and stored for later use. The cells may be cultured in the presence of host or graft T cells ex vivo and re-introduced into the host. This may have the advantage of the host recognizing the cells as self and better providing reduction in T cell activity.

The dose and the administration frequency will depend on the clinical signs, which confirm maintenance of the remission phase, with the reduction or absence of at least one or more preferably more than one clinical signs of the acute phase known to the person skilled in the art. More generally, dose and frequency will depend in part on recession of pathological signs and clinical and subclinical symptoms of a disease condition or disorder contemplated for treatment with the above-described composition. Dosages and administration regimen can be adjusted depending on the age, sex, physical condition of administered as well as the benefit of the conjugate and side effects in the patient or mammalian subject to be treated and the judgment of the physician, as is appreciated by those skilled in the art. In all of the above-described methods, the cells can be administered to a subject at $1 \times 10^4$ to $1 \times 10^{10}$/time.

The specific examples below are to be construed as merely illustrative, and not limitative of the remainder of the disclosure in any way whatsoever. Without further elaboration, it is believed that one skilled in the art can, based on the description herein, utilize the present invention to its fullest extent.

Preparation of SBR and SBT Cells

The method for activation, purification, and expansion of BLSCs has been described in WO/2007/100845. In this example, BLSCs were purified from blood of a human subject using two methods. The isolated cells were analyzed by flow cytometry. The results are shown in FIGS. 1A-1C and FIGS. 2A-2C. It was found that the two methods yielded $200 \times 10^6$ and $230 \times 10^6$ BLSC/ml blood, respectively.

The purified BLSCs were cultured in StemBios-001. To produce SBR and SBT cells, BLSCs were cultured in a StemBios-002 medium for 2 weeks. Then, the BLSCs were cultured in a StemBios-003 medium containing 0.1 to 20 μM of RA or 1 to 40 nM of TGF-β for over 2~6 weeks. It was found the cultured cells gradually changed their morphology and sizes (FIGS. 6-12). These cells were named SBR and SBT cells respectively.

The SBR and SBT cells were tested for their development-differentiation potentials using standard methods. It was found that they can differentiate into cells derived from all three embryonic germ layers, i.e., ectoderm, mesoderm, and endoderm. It was also found that all or a substantial portion of the cells were $CD10^+$, $CD90^+$, $CD105^+$, and $CXCR4^+$.

RT-PCR Results of SBR, SBT, and BLSCs

Gene expressions of the SBR cells, SBT cells, and BLSCs were examined. Total RNA was isolated from cultured SBR cells or SBT cells (more than 6 millions for each) using a Qiagen RNA extraction kit (Qiagen, CA), Paris kit (Ambion), or RNAzol kit (InvitroGen). The cDNA was prepared from 2.0 μg RNA, using 0.25 ng oligo-(dT)12-18 and reverse transcriptase (Qiagen) following the manufacturer's protocol (Qiagen). However, no detectable RNA could be obtained from more than 100 millions BLSCs.

RT-PCR was performed using the condition of 94° C. (15 seconds), 55° C. (15 seconds), 72° C. (20 seconds) for 30 cycles. The primers for beta-actin were: Forward 5'-ACAAAACCTAACTTGCGCAG-3' Reverse 5'-TCCTG-TAACAACGCATCTCA-3'. The primers for GAPDH were: Forward 5'-AGCCACATCGCTCAGACACC-3' Reverse 5'-GTACTCAGCGGCCAGCATCG-3'. The results are shown in FIG. 13. It was found that beta-actin and GAPDH express in SBR cells and SBT cells, but not BLSCs.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of making a mammalian pluripotent cell population comprising obtaining a plurality of mammalian blastomere-like stem cells (BLSCs);
culturing the BLSCs in a medium containing retinoic acid (RA) or transforming growth factor beta (TGF-β) for a sufficient period of time to produce a pluripotent cell population that is 1-15 micrometers in size and expresses mRNA encoding GAPDH or beta-actin, and identifying and isolating the mammalian pluripotent cell population, wherein the pluripotent cell population differentiates into cells derived from ectoderm, mesoderm and endoderm germ layers.

2. The method of claim 1, wherein the BLSCs are cultured in a medium that contains 0.1 to 20 μM of RA for 2 to 8 weeks.

3. The method of claim 1, wherein the BLSCs are cultured in a medium that contains 2 to 20 nM of TGF-β for 2 to 8 weeks.

4. A composition comprising cultured mammalian cells that (1) are pluripotent, (2) are 1-15 micrometers in size, and (3) express the mRNA encoding GAPDH or beta-actin, and wherein the plurality of cultured cells are $CD10^+$, $CD90^+$, $CD105^+$ and $CXCR4^+$.

5. The composition of claim 4, wherein a first population of the cells are $CD66e^+$.

6. The composition of claim 4, wherein a second population of the cells are $CD66e^-$.

7. The composition of claim 4, wherein the cells are trypan blue staining negative.

8. A cell bank comprising a plurality of compositions of claim 4.

9. The cell bank of claim 8, wherein the cells are human cells.

10. The composition of claim 4, wherein the plurality of cultured cells are produced by:
obtaining a plurality of BLSCs, and
culturing the BLSCs in a medium containing 0.1 to 20 μM of RA for 2 to 8 weeks.

11. The composition of claim 4, wherein the plurality of cultured cells are produced by:
obtaining a plurality of BLSCs, and
culturing the BLSCs in a medium containing 1 to 40 nM of TGF-β for 2 to 8 weeks.

12. The composition of claim 4, wherein the plurality of cultured cells are $CD10^+$, $CD90^+$, $CD105^+$ and $CXCR4^+$.

* * * * *